US005728804A

United States Patent [19]

Sharma et al.

[11] Patent Number: 5,728,804
[45] Date of Patent: Mar. 17, 1998

[54] USE OF CYCLODEXTRINS FOR PROTEIN RENATURATION

[75] Inventors: Ajit Sharma; Nadarajah Karuppiah, both of Mount Pleasant, Mich.

[73] Assignee: Research Corporation Technologies, Inc., Tucson, Ariz.

[21] Appl. No.: 460,234

[22] Filed: Jun. 2, 1995

[51] Int. Cl.[6] .............................. C07K 1/00; C12P 21/06
[52] U.S. Cl. .......................... 530/350; 530/351; 530/399; 530/414; 530/417; 514/21; 435/69.1; 435/69.4; 435/69.5; 435/158
[58] Field of Search .................................. 530/350, 351, 530/399, 414, 417; 514/21; 435/69.1, 69.4, 69.5, 188

[56] References Cited

U.S. PATENT DOCUMENTS

| | | | |
|---|---|---|---|
| 3,888,738 | 6/1975 | Okada et al. | 195/66 R |
| 4,511,502 | 4/1985 | Builder et al. | 260/112 R |
| 4,511,503 | 4/1985 | Olsen et al. | 260/112 R |
| 4,518,526 | 5/1985 | Olson | 260/112 R |
| 4,956,274 | 9/1990 | Khamma et al. | 435/188 |
| 4,961,969 | 10/1990 | Hershenson et al. | 435/69.51 |
| 5,466,781 | 11/1995 | Dorin et al. | 530/351 |
| 5,563,057 | 10/1996 | Gellman | 435/188 |

FOREIGN PATENT DOCUMENTS

WO 87/02673  5/1987  WIPO.

OTHER PUBLICATIONS

Gary Williamson et al., "O–Glycosylation and Stability—Unfolding of lycoamylase Induced by Heat and Guanidine Hydrochloride," *Eur. J. Biochem.*, 207, 661–670 (1992).

Burgess–Cassler, A., "Some Observations on Cyclodextrin–Mediated Boosting of Secreted Amylolytic Enzymes by Lactobacillus amylovorus," *Current Micriobiology*, 27, 199–204 (1993).

Cleland, J. L., et al., "Polyethylene Glycol Enhanced Protein Refolding," *Bio/Technology*, 110, 1013–1019 (1992).

Cleland, J. L., et al., "Cosolvent Assisted Protein Refolding," *Bio/Technology*, 8, 1274–1278 (Dec. 1990).

Cleland, J. L., "Impact of Protein Folding on Biotechnology," In: *Protein Folding: In Vivo and In Vitro*, Cleland, J. L., (ed.), American Chemical Society, pp. 1–23 (1993).

Cooper, A., "Effect of Cycldextrins on the Thermal Stability of Globular Proteins," *J. Am. Chem. Soc.*, 114, 9208–9209 (1992).

De Bernardez–Clark, E., et al., "Inclusion Bodies and Recovery of Proteins from the Aggregated State," In: *Protein Refolding*, Georgio, G., et al., (eds.), American Chemical Society, pp. 1–21 (1991).

Florance, J., et al., "Chiral High–Performance Liquid Chromatography of Aromatic Cycle Dipeptides Using Cyclodextrin Stationary Phases," *J. Chromatography*, 543, 299–305 (1991).

Florance, J., et al., "High–Performance Liquid Chromatographic Separation of Peptide and Amino Acid Stereoisomers," *J. Chromatography*, 414, 313–322 (1987).

Makhatadze, G. I., et al., "Protein Interactions with Urea and Guanidinium Chloride—A Calorimetirc Study," *J. Molecular Biology*, 226, 491–505 (1992).

Mathupala, S. P., et al., "Improved Purification and Biochemical Characterization of Extracellular Amylopullulanase from Thermoanaerobacter ethanolicus 39E," *Applied Microbiology and Biotechnology*, 39, 487–493 (1993).

Mikami, B., et al., "The 2.0–A Resolution Structure of Soybean β–Amylase Complexed with α–Cyclodextrin," *Biochemistry*, 32, 6836–6845 (1993).

Nguyen, L. H., et al., "Overproduction and Purification of $\delta^{32}$, the *Escherichia coli* Heat Shock Transcription Factor," *Protein Expression and Purification*, 4, 425–433 (1993).

Puri, N., et al., "Solubilization of Growth Hormone and Other Recombinant Proteins from *Escherichia coli* Inclusion Bodies by Using a Cationic Surfactant," *Biochemical J.*, 285, 871–879 (1992).

Rozema, D., et al., "Artificial Chaperones: Protein Refolding via Sequential Use of Detergent and Cyclodextrin," *J. Am. Chem. Soc.*, 117, 2373–2374 (1995).

Sharma, A., et al., "Enzymatic Clarification of Hyperlipidemic Specimens–Its Rationale and Limits," *Microchemical J.*, 39, 86–98 (1989).

Sharma, A., et al., "Flocculation of Lipids with Cyclodextrins: Applications in the Analysis of Lipemic Serum," *Clinical Chemistry*, 36, p. 1121, Abstract No. 0788 (1990).

Sharma, A., et al., "Flocculation of Serum Lipoproteins with Cycodextrins: Applications to Assay of Hyperlipidemic Serum," *Clinical Chemistry*, 36, 529–532 (1990).

Sharma, A., et al., "Lipoprotein–Cyclodextrin Interaction," *Clinica Chimica Acta*, 199, 129–138 (1991).

Shing, Y., et al., "Affinity of Fibroblast Growth for β–Cyclodextrin Tetradexasulfate," *Analytical Biochemistry*, 185, 108–111 (1990).

Subbaramiah, K., et al., "Affinity Purification of Amylases on Cyclodextrin–Sepharose Columns," *Starch/Starke*, 41, 357–359 (1989).

Vilette, J. R., et al., "Fast Purification of Cyclodextrin–Glucosyltransferase from *Bacillus cirulans* E192 by Affinity Chromatography Using an Epichlorhydrin–Reticulated Copolymer of Beta–Cyclodextrin," *Chromatographia*, 32, 341–344 (1991).

Zardeneta, G., et al., "Micelle–Assisted Protein Folding—Denatured Rhodanese Binding to Cardiolipin–Containing Lauryl Maltoside Micelles Results in Slower Refolding Kinetics but Greater Enzyme Reactivation," *J. Biological Chemistry*, 267, 5811–5816 (1992).

Zejtli, J., "Cyclodextrins in Drug Formulations: Part II," *Pharm. Technol. Int.*, 3, 16–19 (1991).

*Primary Examiner*—Cecilia J. Tsang
*Assistant Examiner*—Abdel A. Mohamed
*Attorney, Agent, or Firm*—Schwegman, Lundberg, Woessner & Kluth, P.A.

[57] ABSTRACT

A method for renaturing a denatured protein is provided comprising contacting a solution or suspension of said denatured protein in a detergent-free liquid medium with an amount of a cyclodextrin effective to renature said protein, and optionally, recovering the renatured protein in essentially pure form.

10 Claims, 6 Drawing Sheets

USE OF CYCLODEXTRINS FOR PROTEIN RENATURATION

BACKGROUND OF THE INVENTION

Protein function is dependent on its three dimensional structure. When a protein is synthesized in a mammalian cell, it first appears essentially as a linear polypeptide chain. The immature chain then folds under appropriate cellular conditions (pH, ionic strength, etc.), sometimes with the help of protein folding catalysts called molecular chaperones, which are proteins themselves. Out of thousands of possible three dimensional shapes, an average mature protein assumes only one conformation, which is often referred to as the native structure of the protein. Any alteration in this native structure may lead to loss of the protein's biological activity, a phenomenon called denaturation. Since the native structure is maintained mostly by weak forces (hydrogen bonding, electrostatic and hydrophobic interactions), proteins can easily be denatured by small changes in their environment. Thus protein denaturation occurs in their purification, storage, use, and transport. A given protein sample may therefore contain appreciable amounts of denatured, inactive protein besides the active, functional form.

With the growth of the biotechnology industry and the increased production of recombinant proteins, interest in the mechanisms by which a protein adopts its native conformation, has increased dramatically. A number of therapeutic proteins are currently being produced by recombinant DNA technology. Examples of such biopharmaceuticals include insulin for treatment of diabetes, human growth hormone for treatment of dwarfism, antibody OKT 3 for reversal of kidney transplant rejection, tissue plasminogen activator for treatment of heart attacks and strokes, DNase for cystic fibrosis and interleukin 2 for chemotherapy. These proteins are presently produced by incorporating a copy of the human gene encoding a particular protein into a rapidly dividing host cell such as a bacterium. The genes are then transcribed into mRNA and translated into protein by the host cell.

The cellular environment of a human cell however, is very different from that of a bacterium, and the production of human protein pharmaceuticals in bacteria by genetic engineering often results in the accumulation of improperly folded proteins (called inclusion bodies) which have little or no biological activity. See, for example, J. L. Cleland, ed., *Protein Folding, In Vivo and In Vitro*, ACS Syrup. Series, 526 (1993). The current hypothesis of protein folding involves the formation of one or more intermediates from the unfolded protein. These intermediates seem to possess some secondary structure and often associate to form soluble aggregates. The soluble protein aggregates can agglomerate to form large irreversible precipitates which appear as "inclusion bodies" in bacterial cells. All intermediates as well as the unfolded protein can form misfolded intermediates that can reduce the yield of the native protein by becoming a kinetic trap for the preceding species. There is considerable evidence that the intermediates have many hydrophobic amino acid residues exposed to the surface which causes their aggregation. These proteins, after isolation and purification from the host cells, have to be completely unfolded, or denatured, and subsequently refolded or renatured so that the proteins regain their bioactivity. However, since every protein has a different three dimensional structure, the folding of a protein from a completely unfolded state to the native conformation it requires to be functional, remains a complex problem.

In spite of these problems, bacterial cells are still the major host cells used by most biotechnology companies, since animal cells are harder to grow in vitro, and isolation and purification of the desired protein is much more difficult and expensive. See, G. Georgiou et al., eds., *Protein Refolding*, ACS Symp. Series 470, ACS (1991).

Refolding processes involve dispersing the protein inclusion bodies in a buffer in the presence of "refolding aids," which can interact with the protein to enhance its renaturation. J. L. Cleland et al., *Biotechnology*, 10, 1013 (1992), have reported that polyethylene glycol enhances refolding yields, and various sugars and detergents have also been employed in refolding. For example, see G. Zardeneta et al., J. Biol. Chem., 267, 5811 (1992); N. F. Puri et al., *Biochem. J.*, 285, 871 (1992); and L. H. Nguyen et al., *Protein Expression Purif.*, 4, 425 (1993). Recently, D. Rozema et al., *J. Amer. Chem. Soc.*, 117, 2373 (1995), reported that sequential complexation of denatured carbonic anhydrase B with a quaternary amine detergent, CTAB, followed by addition of beta-cyclodextrin ($\beta$-CD) to the complex, caused reactivation of the enzyme. The $\beta$-CD was disclosed to strip away the detergent, allowing proper refolding.

While cyclodextrins (CDs) have been reported to be useful in stabilization, solubilization and affinity purification of certain enzymes, both the nature of the interactions between CDs and proteins, and their effect on bioactivity, remain unclear. While CDs have been used to reduce the loss in enzyme activity caused by storage, freeze-drying, heating and oxidizing or dehydrating agents, A. Cooper et al., *J. Amer. Chem. Soc.*, 114, 9208 (1992), reported that CD binding destabilizes certain globular proteins by inducing their defolding. Likewise, in "Cyclodextrins in Drug Formulations, Part II," *Pharm. Technol. Int.*, 3 (1991), it is disclosed that addition of a CD to an aqueous solution of a protein eventually allows the CD to "deaggregate, solubilize, stabilize or eventually denature the dissolved protein molecule, thus modifying its hydration."

Therefore, a continuing need exists for folding aids that are inexpensive, inhibit protein aggregation without inhibiting formation of the native protein, and are easily separated from the refolded protein.

SUMMARY OF THE INVENTION

The present invention provides a method for renaturing ("refolding") a denatured ("unfolded" or aggregated) protein comprising contacting said protein in an aqueous medium with an amount of a cyclodextrin (CD) effective to renature said protein. The aqueous solution may be buffered, e.g., to about pH 6–9, with a Tris salt, but is free of other refolding aids, including detergents, sugars or polyols, including polyethylene glycol. The protein may be in solution or partially or wholly in the form of suspended aggregates, and the term "in an aqueous medium" encompasses all of these forms.

The reaction occurs readily under essentially ambient temperatures (10°–40° C.), although higher temperatures may be employed for thermally-resistant proteins. After a sufficient period of time, e.g., about 1–48 hours or longer, at least about 75% of the initial or theoretical activity of the enzyme, hormone, cytokine or other protein is attained, and recoveries of up to 95–100% have been accomplished. In the case of protein mixtures comprising both inactive and active forms of the protein, recovery of more than 100% of the initial activity of the mixture can be realized.

The protein can then be employed for its end use in solution, or recovered from solution, either in combination with the CD or in essentially pure form. If desired, cyclodextrin can be removed from the aqueous solution, and the protein can be recovered by freeze drying, filtration, chromatography and the like.

Although not intending to be bound by any theory of action, it is believed that the CD forms weak; reversible non-covalent complexes with hydrophobic sites present in partially refolded protein intermediate(s). The relatively polar cyclodextrin molecules that are weakly bound to hydrophobic sites in the folding intermediate(s), are gradually removed as the interior of the protein becomes increasingly non-polar during protein refolding. In addition, the low molecular weight of cyclodextrins allows them ready access to and from the interior of the protein during refolding.

Since the cyclodextrins can inhibit aggregation without interfering with protein refolding, they are highly effective protein folding agents. In addition, CDs are relatively inexpensive, commercially available and are easily separated, if desired, from the refolded protein by dialysis or gel filtration.

DETAILED DESCRIPTION OF THE INVENTION

Figure 1:
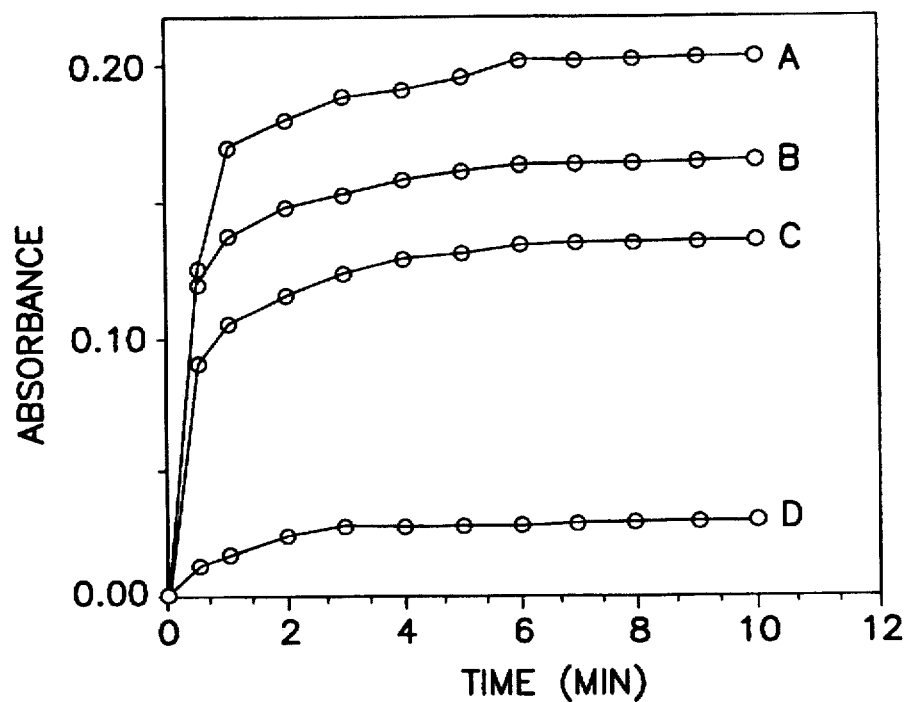
FIG. 1 is a graph depicting the aggregation kinetics in the absence and presence of cyclodextrins. Native enzyme (33 mM) was denatured overnight in 6.8M GuHCl. In each case, protein was diluted to 1.7 µM and 0.034M GuHCl, with renaturation buffer, containing 50 mM CD. Curve A (absence of CD), Curve B ($\gamma$-CD), Curve C ($\beta$-CD), and Curve D ($\alpha$-CD).

Cyclodextrins (CDs) are low-molecular weight, non-toxic macromolecules comprising 6–8 $\alpha$-1,4-linked glucose units.

CDs are formed from the bacterial degradation of starch. The most common CDs reported in literature are the $\alpha$, $\beta$, and $\gamma$ forms, which comprise 6, 7, and 8 glucose monomers, respectively. Modified cyclodextrins are available to the art, and can also be used in the present method, including methylated CDs (DIMEB), hydroxypropyl $\beta$-CD (HPBCD), hydroxymethylated $\beta$-CD, branched CDs comprising 1–2 glucose or maltose residues attached to the CD ring; ethyl- and ethyl-carboxy-methyl-CDs and dihydroxypropyl CDs. Thus, as used herein, the term "cyclodextrin" encompasses such modified CDs, as well as other known CDs and their derivatives.

The internal cavity, ca. 6–10 Å, which is hydrophobic in nature, is a key feature of the cyclodextrin molecule, providing the ability to complex and contain a variety of guest molecules, such as aliphatics, aromatics, fatty acids, and the like, as "inclusion complexes." Aromatic amino acids, such as tryptophan and phenylalamine, are known to form weak inclusion complexes with CDs. See, K. P. Wong et al., *J. Biol. Chem.*, 248, 8518 (1973). In the pharmaceutical industry, cyclodextrins are used for drug stabilization, enhancement of solubility and bioavailability, and conversion of liquid drugs to powders. CDs, their derivatives and polymers have also found important applications in the food and cosmetic industries, in chromatography and photochemistry.

Peptides

A wide variety of naturally-occurring and synthetic proteins, including polypeptides and oligopeptides (dipeptides, tripeptides, tetrapeptides, etc.) can be renatured or refolded in accord with the present method.

The present method may be employed to refold or renature both the simple proteins and conjugated proteins. Simple proteins include the naturally-occurring proteins which yield only alpha-amino acids or their derivatives on hydrolysis. They are of several types and include:

(a) Albumins, which are soluble in water and coagulated by heat; e.g., ovalbumin in egg white and serum albumin in blood.

(b) Globulins, which are insoluble in water but soluble in dilute salt solutions and coagulable by heat; e.g., serum globulin in blood, purified antibody preparations, including monoclonal antibodies, fragments of monoclonal antibodies including recombinant mammalian binding regions, i.e., chimetic murine-human antibodies.

(c) Glutelins, which are insoluble in water or dilute salt solution but soluble in dilute acid and alkali; e.g., glutenin in wheat.

(d) Prolamines, which are insoluble in neutral solutions but soluble in 80% alcohol; e.g., zein in corn and gliadin in wheat.

(e) Albuminolds, which are dissolved only by boiling in strong acids; e.g., keratins in hair and horny tissue, elastins in tendons and arteries, and collagens in skin and tendons.

(f) Histones, which are basic in reaction, soluble in water but insoluble in dilute ammonia, and difficultly heat-coagulable; e.g., thymus histone.

(g) Protamines, which are strongly basic in reaction and soluble in water, dilute acid, and ammonia; e.g., salmin and sturin in fish sperm.

Conjugated proteins include those proteins which are combined with some nonprotein substance. The classes include:

(a) Phosphoproteins—contain a phosphoric acid moiety as the prosthetic group, e.g., casein in milk and ovovitellin in egg yolk.

(b) Nucleoproteins—the nonprotein portion is a nucleic acid; e.g., nuclein in cell nuclei.

(c) Glycoproteins—simple proteins linked to a carbohydrate group; e.g., mucins in vitreous humor and saliva, lectins in plants, viral glycoproteins, such as HIV, HCMV and HBV glycoproteins, and erythropoietin.

(d) Chromoproteins—contain a colored prosthetic group; e.g., hemoglobin in blood, and flavoproteins.

(e) Lipoproteins—proteins in combination with lipid materials such as sterols, fatty acids, lecithin, etc. These include lipoprotein a, high-density lipoprotein cholesterol (HDL-cholesterol) and low-density lipoprotein cholesterol (LDL-C).

(f) Metalloproteins—the prosthetic group contains a metal; e.g., enzymes such as tyrosinase, arginase, xanthine oxidase, and non-enzymes such as hemoglobin.

(g) Fusion proteins, which are hybrids of different proteins obtained by methods of genetic engineering.

Enzymes are polypeptides which may be classified under six general groups: hydrolases, oxidoreductases, transferases, lyases, isomerases, and ligases. The first group, hydrolase enzymes, include proteolytic enzymes, which hydrolyze proteins, e.g., elastase, papain, ficin, pepsin, trypsin, chymotrypsin, bromelin, and keratinase; carbohydrases, which hydrolyze esters, e.g., lipase, carbonic anhydrase, cholinesterase, lecithinase, and phosphatase; nucleases, that hydrolyze nucleic acid, e.g., ribonuclease and deoxyribonuclease; and amidases, which hydrolyze amines, e.g., arginase, asparaginase, glutaminase, and urease. The second group are redox enzymes, which catalyze oxidation or reduction reactions. These include glucose oxidase, catalase, peroxidase, lipoxidase, and cytochromes. The third group are transferase enzymes, which transfer groups from one molecule to another. Examples of these are glutamic-pyruvic transaminase, glutamic-oxalacetic transaminase, transmethylase, phosphopyruvic transphosphorylase, and dehydrogenase. The fourth group are lyase enzymes, which catalyze the cleavage of C—C, C—O, C—N and other bonds by elimination, leaving double bonds, or conversely, adding groups to double bonds. Examples of these are carbonic anhydrase, pyruvate decarboxylase, amino acid decarboxylase, aldolase, fumarate hydratases, aconitate hydratases, and ammonia lyase. The fifth group are isomerase enzymes, which catalyze the dehydrogenation and epimerization of amino acids and sugars. An example of an isomerase is phosphoglucomutase. The sixth group are ligase enzymes, which catalyze the synthetic linking of two molecules, simultaneously with the breakdown of ATP. Examples of these are aminoacyl-tRNA synthetases and biotinyl-dependent carboxylases.

Chemotactic peptides, which are involved in the mechanisms of chemoattraction, can also be renatured, e.g., the monocyte attractor, N-formyl-Met-Leu-Phe-benzyl ester. See, P. P. Ho et al., *Arthritis Rheum.*, 21, 133 (1978). Immunomodulators and mammalian cell growth factors can also be cleaved in accord with the invention. They include cytokines, e.g., lymphokines, such as the interleukins, and the hematopoietic growth factors such as colony-stimulating factors, GM—CSF, M—CSF, G—CSF, ED—CSF, MCGF and the like. See, *Hematopoiesis*, D. W. Golde, Ed., Churchill Livingstone, N.Y (1984) at pages 203–244.

The polypeptide hormones can also be renatured in accord with the present method. These include the pituitary, parathyroid, and pancreatic hormones. Pituitary hormones include growth hormone releasing factor, somatotropin or human growth hormone, somatostatin, follicle-stimulating hormone, luteinizing hormone, human thorionic gonadotropin, thyrotropin, corticotropin (ACTH.) hypothalamic hormone, and the like. Pancreatic hormones include pancreatic glucagon, insulin, amylin, and pancreastatin.

The endorphins, e.g., α-endorphin and β-endorphin, can also be renatured using the present methods, as can neuropeptide K and methionine-containing enkephalin analogs such as proenkephalin. A number of the gastrointestinal peptides can also be renatured. They include gastrin-related peptide, carerulein, galanin message associated peptide (1–41), motilin, gastric inhibitory polypeptide, gastrin I, minigastrin I, gastrin releasing peptide, vasoactive intestinal peptide (porcine), and the like.

Other bioactive peptides that can be refolded include insulin, melanocyte stimulating hormones, opioid peptides such as adrenal peptide E and bovine adrenal medulla docosapeptide, oxytocin, isotocin, vasopressin, conotoxin, endothelin, epidermal growth factor brain natriuretic peptide, magainin I, magainin II, molluscan excitatory peptide, molluscan cardioexcitatory neuropeptide, transforming growth factor-α, α-SK-2-mating factor and urotensin.

Bioactive subunit peptides, which are formally subunits of these proteins and polypeptides, may also be renatured using the method of the invention.

For a more extensive listing of bioactive peptides including literature citations, see *ICN Biochemicals Catalog*, ICN Biomedicals, Inc., Irvine, Calif. (May 1992–1993) at pages 985–1030, and *Biochemicals and Organic Compounds for Research and Diagnostic Reagents*, Sigma Chemical Co., St. Louis (1989) at pages 282–325.

Commercially-important proteins which can be refolded using the present method include recombinant insulin and its subunits, human growth hormone, tissue plasminogen activator, the interferons, including gamma-interferon, colony stimulating factors such as G-CSF and cMpl, and human deoxyribonuclease, which is used to treat cystic fibrosis.

The amount of protein in the aqueous medium, and the amount of CD (or a mixture of CDs) may be varied widely, as exemplified herein below. Amounts of CD equal to about 5–10weight % of the protein have been found to be effective, while the protein is present at concentrations selected to minimize aggregation, preferably at less than about 1 mg/ml.

The aqueous medium is preferably water, which is preferably buffered to the desired pH. The medium may contain minor but effective amounts of organic cosolvents, such as alkanols, to assist dissolution of the protein or CD, or alkali metal salts, such as halides, to adjust ionic strength. However, the medium preferably does not comprise any other known folding agents, either solid or liquid. Thus, the present method can be defined as "consisting essentially of" contacting the dissolved or suspended protein with the CD(s). Although the proteins which are renatured are typically 100% denatured, or unfolded, prior to refolding, protein solutions or suspensions which retain some degree of activity can also be employed in the present method. Thus, the present media can contain some renatured or partially folded proteins, in addition to the completely unfolded proteins or aggregates thereof.

The invention will be further described by reference to the following detailed examples wherein carbonic anhydrase II (from bovine erythrocytes, also designated as carbonic anhydrase B or CAB) and p-nitrophenol acetate were obtained from Sigma Chemical Co. (St. Louis, Mo.). Alpha-cyclodextrin, hydroxypropyl beta-cyclodextrin and gamma-cyclodextrin were obtained from American Maize-Products Company (Hammond, Ind., USA). Guanidine hydrochloride (GuHCl) was obtained from Life Technologies, Inc. (Gaithersburg, Md.).

The concentration of native CAB proteins in 50 mM Tris-sulfate at pH 8.5 was determined by its absorbance at 280 nm and using an extinction coefficient of 1.83 (mg/ml protein)$^{-1}$ cm$^-$ and a molecular weight of 30,000 (K. P. Wong et al., *J. Biol. Chem.*, 248, 8518 (1973)).

The enzymatic esterase activity of CAB was measured by its hydrolysis of the substrate, p-nitrophenol acetate (50 mM Tris-sulfate, pH 7.5, concentration of substrate in assay mixture was 1 mM), to form p-nitrophenol, which was monitored at 400 nm and at 25° C. in a double-beam spectrophotometer (Beckman Model 34). Assays were performed at pH 7.5 since the blank rates increase appreciably at higher pH. At the concentrations used in this investigation, there was no significant hydrolysis of the substrate by any of the three CDs.

Turbidimetric analysis of protein aggregation was performed at 400 nm and 25° C. on the Beckman Model 34 spectrophotometer, and fluorescence spectra were obtained with a Perkin Elmer Luminescence Spectrometer LS50B.

Carbonic anhydrase was denatured by overnight incubation in 5–7M GuHCl in 20 mM Tris-sulfate, pH 8.5 at 25° C. Protein inactivation was confirmed by enzymatic activity as well as fluorescence measurements. Refolding studies of carbonic anhydrase were conducted by rapid dilution of the CAB-containing solution in renaturation buffer consisting of 50 mM Tris-sulfate, pH 8.5, with or without added CD.

Example 1. Aggregation Inhibition Studies

When denatured CAB in GuHCl was rapidly diluted with 50 mM Tris-sulfate buffer at pH 8.5, to 1.7 µM protein and 0.03 M GuHCl, aggregation was observed immediately and was monitored by light scattering at 400 nm (FIG. 1, curve A). Aggregation increased with time and then stabilized after approximately 5 minutes. When the denatured protein was renatured in the presence of CDs under the same conditions, light scattering due to aggregation was significantly reduced. The ability of cyclodextrins to inhibit CAB aggregation was in the order of α-CD>hydroxypropyl β-CD<γ-CD (FIG. 1, curves D, C, and B, respectively). Inhibition of CAB aggregation was enhanced with increasing concentration of cyclodextrin in the renaturation buffer (data not shown).

Example 2. Reactivation of CAB with CDS.

Figure 2:
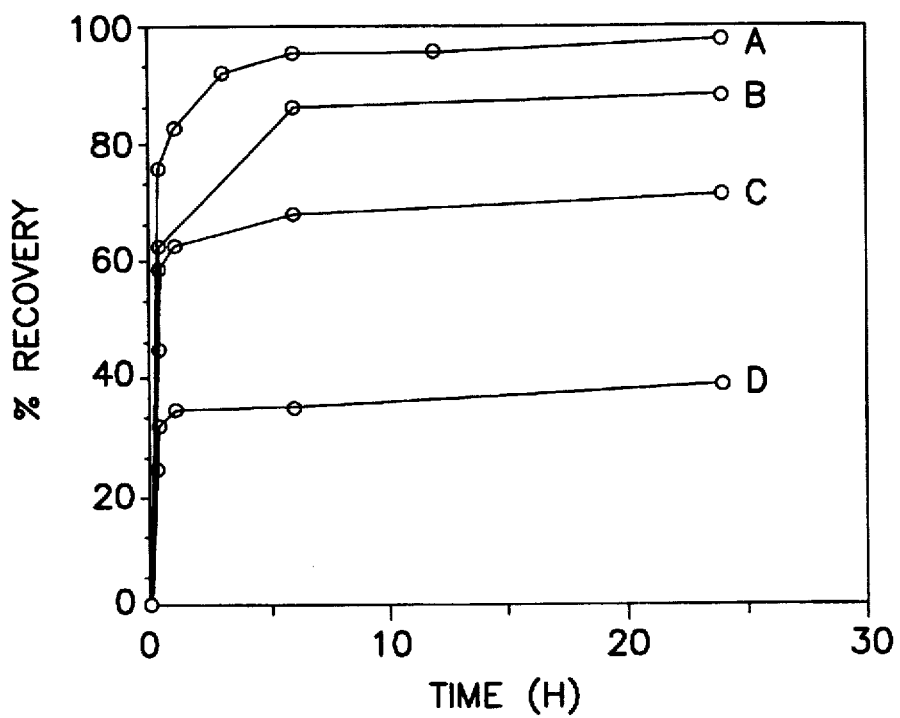
FIG. 2 is a graph depicting the reactivation kinetics in the presence of cyclodextrins. Denatured CAB (333 µM) was diluted to 17 µM protein and 0.34M GuHCl with 50 mM Tris-sulfate buffer, pH 8.5, containing 100 mM cyclodextrin. Curves A, B, C show the renaturation kinetics obtained with $\alpha$-CD, $\beta$-CD, and $\gamma$-CD, respectively. Control without cyclodextrin is shown as Curve D.

Typical results of the reactivation kinetics of CAB at aggregating conditions (17 µM CAB, 0.34M GuHCl) in the presence of alpha, beta, and gamma-cyclodextrins are shown in FIG. 2. Denatured CAB in GuHCl was diluted with renaturation buffer containing 100 mM CD at 25° C. Recovery of esterase activity (compared to the native enzyme) was then measured as a function of time after dilution. The rate of renaturation was rapid in the first few minutes and then gradually reached a plateau within 6 hours of renaturation. Highest recovery of activity was achieved with α-CD, followed by hydroxypropyl β-CD and γ-CD (FIG. 2, curves A, B, and C, respectively). In the absence of cyclodextrin, the recovery of enzyme activity is only about 40% (FIG. 2, curve D). Alpha-cyclodextrin at 100 mM gave over 80% recovery in less than an hour.

Example 3. Renaturation with Varying Amounts of α-CD.

Figure 3:
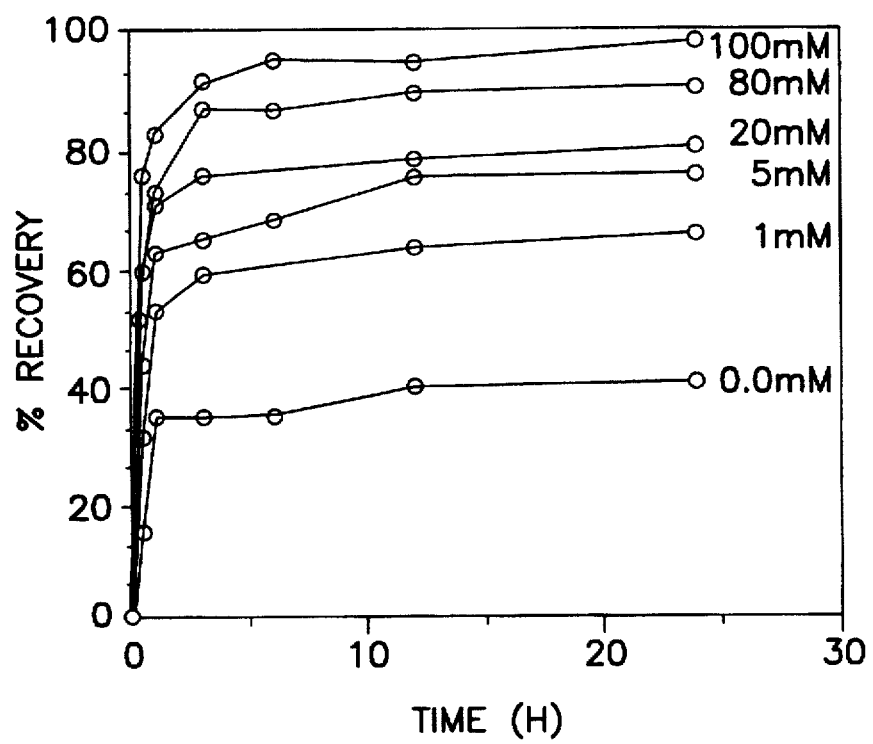
FIG. 3 is a graph depicting the refolding kinetics in the presence of varying amounts (0–100 mM) of $\alpha$-CD. Conditions for denaturation/renaturation are similar to those described in FIG. 2. In each case, CAB concentration during renaturation was 17 µM.

CAB renaturation kinetics in the presence of varying amounts of α-CD (0–100 mM) in the dilution buffer was assessed at 17 µM protein and 0.34M GuHCl (FIG. 3). Although the initial rates of recovered activity did not increase appreciably, the final yields of reactivated enzyme obtained, however, increased with increasing amounts of alpha-CD.

Example 4. Renaturation—Effect of Protein Concentration

Figure 4:
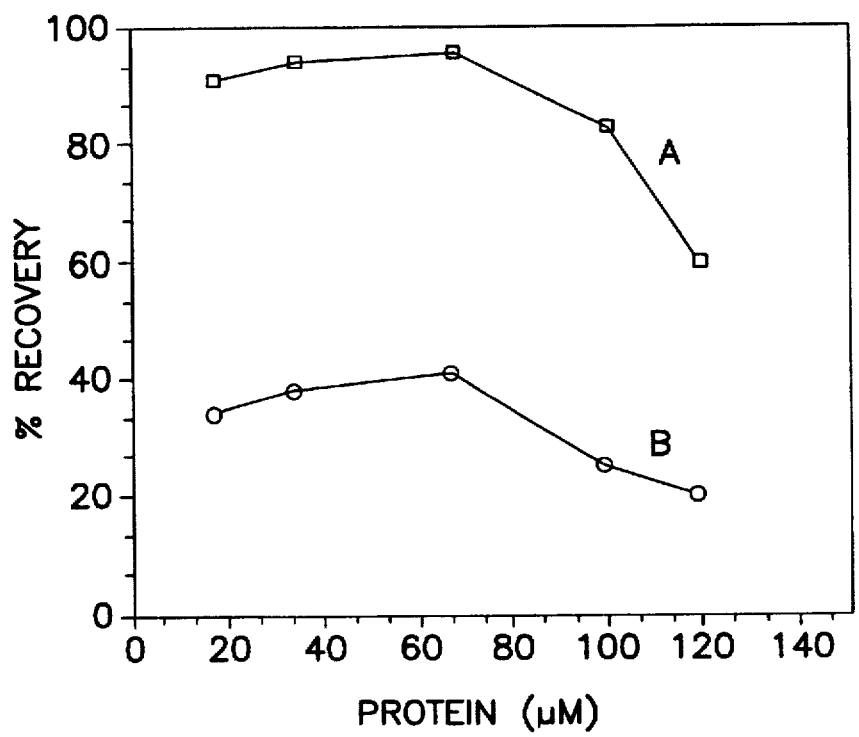
FIG. 4 is a graph depicting the effect of protein concentration on the refolding kinetics of CAB. Native protein (1.2 mM) was denatured in 6.8M GuHCl overnight. The denatured enzyme was diluted to 17–122 µM protein and 0.68M GuHCl. Curve A represents enzyme recovery obtained with 100 mM $\alpha$-CD while Curve B represents recovery obtained in its absence.

Effect of protein concentration on reactivation efficiency at 0.1M alpha-CD is shown in FIG. 4. In each case, refolding was allowed to occur for 6 hours. Over 90% recovery was obtained for CAB concentration as high as 67 µM. Recovery of active protein decreased at higher protein concentrations due to increased protein aggregation.

The effect of pH and temperature on cyclodextrin assisted CAB refolding is summarized in Table 1. In each case, the enzyme was refolded by dilution to 17 µM protein and 0.34 GuHCl for 6 hours. Optimal yield of active protein was obtained between 25° C.–37° C. and under alkaline conditions.

TABLE 1

Effect of pH and temperature on CD enhanced CAB refolding

| | | % Recovery | |
|---|---|---|---|
| pH | Temp (°C.) | −αCD | +αCD |
| 8.5 | 4 | 19 | 75 |
| 8.5 | 25 | 30 | 90 |
| 8.5 | 37 | 32 | 95 |
| 8.5 | 50 | 0 | 1 |
| 5.0 | 25 | 0 | 0 |
| 6.0 | 25 | 14 | 65 |
| 7.0 | 25 | 30 | 87 |
| 8.0 | 25 | 28 | 88 |
| 9.0 | 25 | 24 | 84 |

Example 5. Recovery of Activity in Excess of Initial Activity

A given sample of protein may contain both active and inactive protein. The inactive protein may be present due to denaturation during protein purification and/or storage. If such a sample were subjected to refolding by the present method, then recovery of the activity of the inactive protein, in addition to the activity of the initially active protein, can yield greater than 100% recovery of activity.

Four vials of carbonic anhydrase solid (lyophilized) were obtained from Sigma Chemical Co. (cat. #C2522 p. 211 of 1995 Sigma catalog). Each vial should contain functional (active) and some amount of non-functional (inactive) protein, as explained above.

Buffer (50 mM Tris-sulfate, pH 8.5) was added to each vial. The amount of active carbonic anhydrase was determined by assaying for the enzyme by its esterase activity. This is given a value of 100% in Table 2.

To each vial was added guanidinium hydrochloride so that the final concentrations were as follows: Protein concentrations in vials 1–4 were 4.3 mg/mL, 6.2 mg/mL, 9.6 mg/mL, and 10.6 mg/mL, respectively. Guanidinium hydrochloride concentration in all vials was 6.0M.

The vials were incubated overnight at room temperature. Under these conditions, all the protein (inactive and active) is completely unfolded.

The unfolded protein was then refolded in the presence of cyclodextrin at different protein concentrations. To each vial was added buffered alpha-cyclodextrin (10% w/v alpha-cyclodextrin in 50 mM Tris-sulfate buffer, pH 8.5). The final protein concentration in each vial is given in Table 2. The final guanidinium hydrochloride concentration in all vials was 0.3M. The vials were incubated for 30 hours at room temperature. The amount of active protein was again determined by its esterase activity and compared to that obtained initially. The results are shown on Table 2, below.

TABLE 2

| Vial # | Original enzyme activity in vial | Protein concentration during refolding (mg/mL) | Enzyme activity of refolded protein |
|---|---|---|---|
| 1 | 100% | 0.22 | 144% |
| 2 | 100% | 0.3 | 145% |
| 3 | 100% | 0.48 | 109% |
| 4 | 100% | 0.53 | 110% |

The results above indicate that protein present in the commercially-available sample was a mixture of active (correctly folded) and inactive (denatured or incorrectly folded) forms. The amount of inactive protein in a sample may vary depending on the purification scheme, storage and transport conditions. Thus, the present refolding method is useful to recover the inactive form present in a sample of protein.

Example 6. Competitive Complexation.

Figure 5:
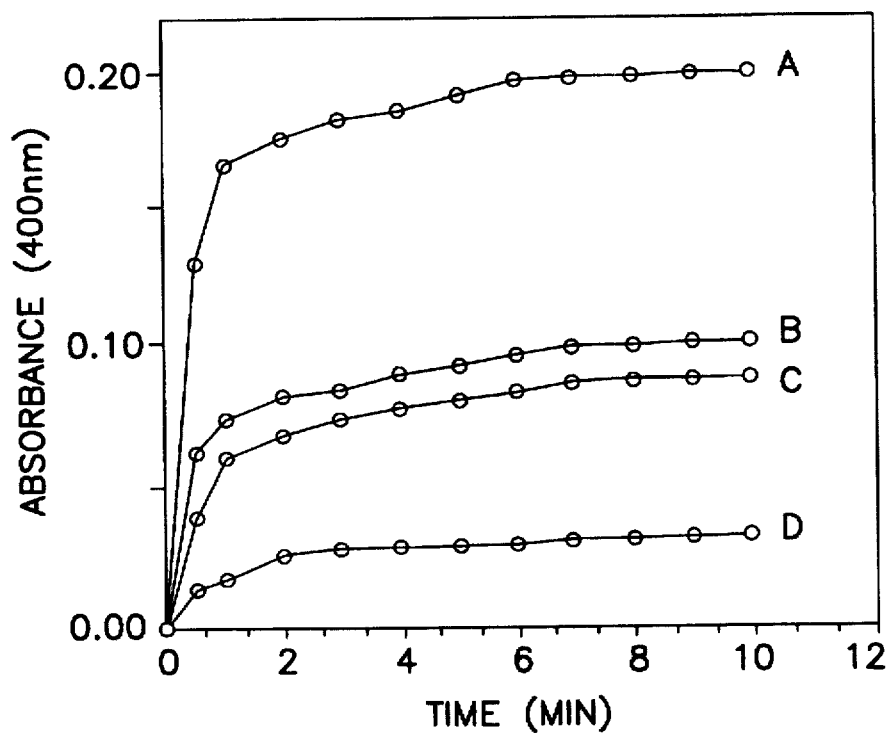
FIG. 5 is a graph depicting the aggregation kinetics of CAB in the presence of cyclodextrins and competitors. Denatured CAB was diluted to 1.7 µM protein and 0.034M GuHCl. Curves A and D represent aggregation in the absence and presence of 50 mM $\alpha$-CD, respectively. Curves B and C show aggregation observed in the presence of 50 mM $\alpha$-CD plus competitor (Trp, 2.5 mM and Phe, 3 mM, respectively).

The importance of the interaction between CD and the hydrophobic sites in CAB intermediate(s) is demonstrated by competitive studies shown in FIG. 5. As is the case in FIG. 1, dilution of denatured CAB resulted in aggregate formation which increased light scattering at 400 nm (curve A). When dilution was performed in α-CD, aggregation was inhibited (curve D). However, when dilution was performed in the presence of CD and an aromatic amino acid (Trp, curve B, Phe, curve C), protein aggregation increased. On the other hand, a polar amino acid such as glycine showed no effect on the aggregation kinetics (data not shown). These results suggest that α-CD forms inclusion complexes with exposed hydrophobic sites such as aromatic amino acids present in the protein folding intermediate(s). This "blocking" of the "sticky" sites during CAB refolding by CDs is a possible mechanism of CD-induced inhibition of protein aggregation.

Figure 6:
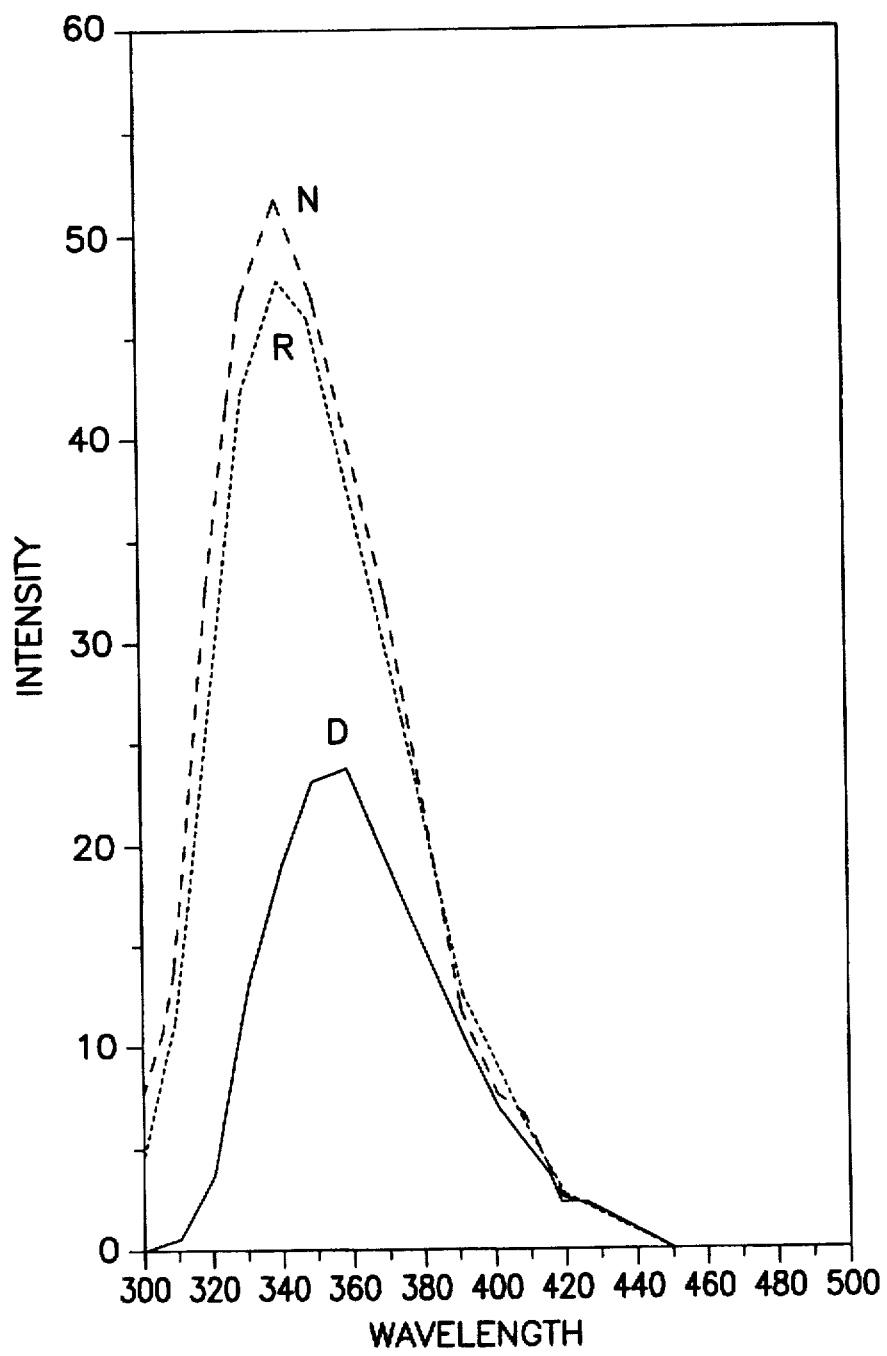
FIG. 6 is a plot of the fluorescence spectra of CAB. Curve N represents the spectrum of the native protein in 50 mM Tris-sulfate, pH 8.5. Curve D represents the spectrum of denatured CAB in 6.8M GuHCl while Curve R is the spectrum of the protein renatured with 100 mM $\alpha$-CD for 1 hour. In each case, the final protein concentration was 0.56 µM. All spectra have been corrected for their respective blanks.

If the CD-folding intermediate interaction was too strong, the CDs will be trapped in the protein as it folds on denaturant removal. That this is not the case is evident from the high recovery of enzyme activity obtained in the presence of cyclodextrin. CD renatured protein also shows identical fluorescence spectra as that of the native enzyme (FIG. 6).

Example 7. Amylase Refolding in the Presence of alpha-Cyclodextrin.

Amylase, obtained from Sigma Chemical Co. (catalogue # A4551) was denatured in a urea/acid mixture (8M urea, 0.1M HCl) for 18 hours. Unfolding was monitored by fluorescence spectra and enzyme activity (3,5-dinitrosalicyclic method of Rick & Stegbauer; in *Methods of Enzymatic Analysis*, H. U. Bergmeyer, ed., Vol. 2, p. 885).

Refolding was carried out with renaturation buffer (0.1M Tris-Cl, pH 8.0) with and without α-CD at room temperature. Protein concentration during refolding was 0.0125–0.2 mg/mL. The recovery of native protein (U/L), obtained after 2 hours of refolding, is summarized on Table 3.

TABLE 3

| Enzyme concentration (mg/mL) | Enzyme activity, U/L Control (minus α-CD) | Enzyme activity, U/L (plus 10% α-CD) |
|---|---|---|
| 0.0125 | 74 | 208 |
| 0.025 | 168 | 381 |
| 0.05 | 228 | 580 |
| 0.1 | 257 | 705 |
| 0.2 | 282 | 950 |

The above data clearly indicates that reactivation of α-amylase is enhanced in the presence of α-cyclodextrin.

Example 8. Amylase Refolding with alpha-Cyclodextrin compared to PEG.

The refolding of α-amylase with α-CD was compared with a well-known protein folding aid, polyethylene-glycol (3% PEG in 50 mM Tris sulfate buffer, pH 8.5). Renaturation was performed at a protein concentration of 0.5 mg/mL using 50 mM Tris sulfate buffer, pH 8.5. These conditions are similar to those employed in the refolding of carbonic anhydrase. Data for this study is shown on Table 4.

TABLE 4

| Enzyme activity, U/L | | | |
|---|---|---|---|
| Control (no folding aid) | PEG (m.w. 8000) | PEG (m.w. 6000) | α-Cyclodextrin (10%) |
| 65 | 70 | 123 | 2025 |

This data demonstrates that α-cyclodextrin is a much better folding agent than a well known folding aid used presently (PEG). Similar results were obtained with carbonic anhydrase.

Example 9. Amylase Refolding with alpha-Cyclodextrin: Effect of Ionic Strength

Urea/acid-unfolded amylase was refolded at 0.2 mg/mL in the presence of buffered cyclodextrin (10% w/v alpha-cyclodextrin in 10 mM Tris sulfate buffer, pH 8.5) containing various amounts of NaCl. The results obtained after one hour of refolding at 25° C. is summarized on Table 5.

TABLE 5

| Sample | NaCl (mM) | Enzyme activity, U/L |
|---|---|---|
| 1. Control (−α-CD) | 0 | 398 |
| 2. Test | 15 | 262 |
| 3. Test | 30 | 297 |
| 4. Test | 60 | 540 |
| 5. Test | 120 | 2426 |
| 6. Test | 480 | 2673 |

This data demonstrates that control of ionic strength can enhance amylase refolding. Other conditions have to be optimized in order to achieve higher refolding yield. However, even under non-optimal conditions, refolding in the presence of cyclodextrin significantly increases the amount of folded protein.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for renaturing a unfolded or aggregated protein comprising contacting said unfolded or aggregated protein in a detergent-free aqueous medium with an amount of a cyclodextrin effective to renature said unfolded or aggregated protein.

2. The method of claim 1 wherein the renatured protein is recovered from said aqueous solution.

3. The method of claim 1 wherein the cyclodextrin is alpha-cyclodextrin, hydroxypropyl-beta-cyclodextrin, or gamma-cyclodextrin.

4. The method of claim 1 wherein the aqueous medium is buffered at about pH 6–9.

5. The method of claim 1 wherein the renaturation is carried out for about 1–48 hours.

6. The method of claim 1 wherein the renaturation is carried out at about 10°–40° C.

7. The method of claim 1 wherein the cyclodextrin is removed from the renatured protein medium by dialysis or filtration.

8. The method of claim 1 wherein the unfolded or aggregated protein is a cytokine or a hormone.

9. The method of claim 1 wherein the unfolded or aggregated protein is an enzyme.

10. The method of claim 9 wherein at least about 75% of the theoretical enzymatic activity is recovered.

* * * * *